(12) United States Patent
Fejfar et al.

(10) Patent No.: US 7,707,002 B2
(45) Date of Patent: Apr. 27, 2010

(54) DEVICE AND METHOD FOR DETERMINING PROCESS STATUS BY TONE VALUE AND COLOR REPRODUCTION MEASUREMENT

(75) Inventors: Florian Fejfar, München (DE); Armin Weichmann, Kissing (DE)

(73) Assignee: MAN Roland Druckmaschinen AG, Offenbach am Main (DE)

( * ) Notice: Subject to any disclaimer, the term of this patent is extended or adjusted under 35 U.S.C. 154(b) by 208 days.

(21) Appl. No.: 11/642,611

(22) Filed: Dec. 19, 2006

(65) Prior Publication Data

US 2007/0144390 A1   Jun. 28, 2007

(30) Foreign Application Priority Data

Dec. 20, 2005   (DE) .................. 10 2005 060 893

(51) Int. Cl.
*B41F 33/00* (2006.01)
(52) U.S. Cl. ................ 702/150; 347/15; 347/19; 358/504; 358/518; 358/1.9
(58) Field of Classification Search ............... 702/150; 355/18, 38, 40, 41, 487, 77; 382/190, 274; 345/207; 347/5, 15, 16, 19; 101/484, 485; 358/504, 518, 1.9
See application file for complete search history.

(56) References Cited

U.S. PATENT DOCUMENTS

| | | | | |
|---|---|---|---|---|
| 4,984,013 | A * | 1/1991 | Terashita | 355/38 |
| 5,551,342 | A * | 9/1996 | Fuchs et al. | 101/484 |
| 5,724,456 | A * | 3/1998 | Boyack et al. | 382/274 |
| 6,459,425 | B1 * | 10/2002 | Holub et al. | 345/207 |
| 6,636,646 | B1 * | 10/2003 | Gindele | 382/274 |
| 6,724,937 | B1 * | 4/2004 | Wu et al. | 382/190 |
| 2002/0135743 | A1 * | 9/2002 | Gindele | 355/18 |

* cited by examiner

*Primary Examiner*—Drew A Dunn
*Assistant Examiner*—Hien X Vo
(74) *Attorney, Agent, or Firm*—Cohen Pontani Lieberman & Pavane LLP (57) ABSTRACT

The present invention concerns measures for the space-optimized determination of printing-related measured values. With the aid of a tone value and/or color gradient in a control patch and a suitable measuring device, it is possible to obtain, in a smaller amount of space, adequate or even detailed information about the printing process. Correcting values necessary for the automatic control of the printing operation can be determined on the basis of the information thus obtained, which can be also be continuously acquired due to the space-optimized tone value and/or color gradients.

21 Claims, 5 Drawing Sheets

DEVICE AND METHOD FOR DETERMINING PROCESS STATUS BY TONE VALUE AND COLOR REPRODUCTION MEASUREMENT

BACKGROUND OF THE INVENTION

1. Field of the Invention

The present invention concerns a device and a method for determining printing-related measured values from a gradient patch printed as a control patch and a corresponding computer program.

2. Description of the Related Art

In the control of printing processes, it is necessary to determine quality-relevant parameters as often as possible in order to manage the printing process according to the determined parameters. Quality-relevant parameters are all parameters that can describe the reproduction of the subject on the medium to be printed, e.g., paper. In particular, it is important to check the reproduction of chromatic and achromatic inks. Examples of quality-relevant parameters are therefore the degree of area coverage or screen tone value that has been achieved, the tone value increase, or the full-tone density achieved with an ink. To determine these parameters, in industrial printing, e.g., in offset printing with a rotary press, print control strips are printed during the printing operation along with the actual printing job. To determine some quality-relevant parameters, for example, the screen tone value or the full-tone density of an ink, control patches are printed by the printing press as part of print control strips.

A control patch is an area printed on the printing medium and contains an image area. In order, for example, in the prior art, to check the screen tone value, several control patches are arranged in a row to form a control patch strip, and the control patches represent a possibly different percentage of area coverage. Due to limited space, as few control patches as possible are usually printed on the prior-art print control strip. For example, the use of three control patches in the form of a tone value wedge with a degree of area coverage of 25%, 50%, and 75% is known. Test charts for determining the tone value increase generally consist of these tone value wedges reproduced in the given process color. However, the test charts known from the prior art allow only imprecise measurement of the tone value increase. In accordance with the prior art, to obtain a more precise measurement over the entire tone value range, the space requirement that would be necessary for exact determination of the tone value increase would increase considerably.

On the basis of the evaluation of the quality-relevant parameters, e.g., the screen tone value or the full-tone density of an ink, the technical personnel can carry out adjustment steps on the printing press to optimize the printing result. These adjustment steps can be automatically carried out in the same way by a suitable device. Customary adjustment steps on an offset press involve metering of the ink and water.

Figure 1:
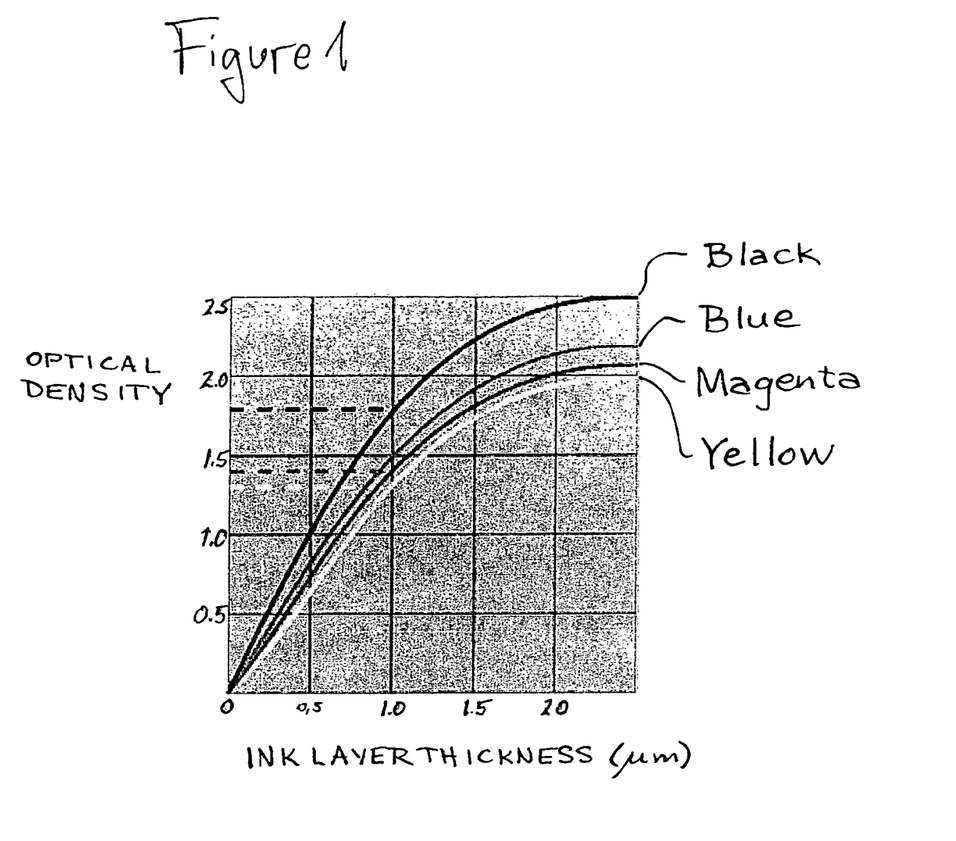
FIG. 1 shows a graph illustrating the relationship between ink layer thickness and optical density for various colors.

The relationship between quality-relevant parameters and adjustment steps is explained below on the basis of the example of the full-tone density of an ink. The full-tone density of an ink is measured by densitometry, i.e., the optical density of an ink is determined in a control patch. The optical density is an important characteristic in the printing process, which is directly related (almost linearly in certain subdomains) to the ink layer thicknesses transferred in the printing process, as FIG. 1 shows. Measurement of the optical density and control of the printing process on the basis of the density values represents a possible means, widely used in the prior art, of maintaining the ink metering constant in the printing process.

Some measurement data of quality-relevant parameters, e.g., the tone value increase, are fed back to the prepress phase in order to achieve control of the printing process. The measurement data are processed in the prepress phase, e.g., into correction curves or an ICC (International Color Consortium) color profile, i.e., generally speaking, they are used in computational steps of the prepress phase.

To determine the parameters for preparing the ICC color profile, the space requirement is considerable for printing technology, since test charts for preparing an ICC color profile normally have a large number of control patches, including not only control patches with the given primary colors but also a great variety of control patches with mixed colors. In this regard, it can be said that the more colors are measured, i.e., the more control patches are available, the more exactly the ICC color profile can be prepared. However, to realize the best possible utilization of the printing press, it is necessary to cover the largest possible portion of the printed area with the actual printing job. The present invention arose from the conflicting interests that have been described, i.e., on the one hand, improved qualitative evaluation of the printing process by the largest possible number of control patches and, on the other hand, the necessity of saving printed area.

SUMMARY OF THE INVENTION

Accordingly, an object of the invention is to provide possible means of determining quality-relevant parameters in the printing process as precisely as possible and with control patches arranged on the printing medium in a way that optimizes space requirements, so that the determination can be made inexpensively.

In accordance with a first aspect of the invention, a measuring unit is provided for determining a printing-related measured value from a tone value and/or color gradient of a control patch. Printing-related measured values are understood to be, for example, measured values such as full-tone density or screen tone value. In this regard, depending on the type of measured value, either a tone value gradient or a color gradient is to be used. In accordance with the invention, a control patch is understood to be a well-defined region in which a gradient is printed. This region is usually provided in a print control strip. However, it is also possible to define a certain region of the subject as a region suitable for a control patch. This can be realized, on the one hand, by a suitable analysis of the subject and, on the other hand, by a systematic incorporation of a control patch into the subject. A gradient is basically understood to mean a transitionless gradient, but a gradient-like control patch is also conceivable, which arranges different tone values or colors in a row in a graduated way, wherein the tone values or colors are so closely graduated that a gradient-like impression is obtained, at least in some subdomains.

The measuring unit has a photosensitive sensor that is position-resolving in at least one direction, a central processing unit, a measuring device for determining a printing-related measured value, and a memory for storing measured values. In accordance with the invention, the measuring device determines not only a printing-related measured value but also a position of a measuring point associated with the measured value.

An example of a position-resolving sensor that can be used is a CCD chip. The only important consideration in the choice of a sensor is that sufficient accuracy of resolution is achieved. An accuracy of resolution of greater than 0.2 mm is regarded as especially advantageous. A central processing unit or CPU is needed to evaluate the data acquired from the position-resolving sensor. Accordingly, a PC can also be used for the data processing, but the use of a digital signal processor integrated in the measuring unit as a compact measuring instrument is preferable for the hardware realization of the measuring unit of the invention. In addition, the measuring unit also has at least one memory, which, for one thing, can temporarily store the data from the sensor and, for another, can store the computational results of the measuring device. The measuring device can be functionalized by means of a computer program, and for each printing-related measured value it also determines the position of the measuring point. If, for example, the density is determined in the gradient patch at a point by means of the measuring unit in the form of a densitometer, the measuring device is additionally able to reference the position of this point to a previously determined point. This common reference point for the measuring points is preferably the left limit, i.e., a starting point of the gradient patch. This measure, i.e., the determination of measuring point position and measured value, makes it possible to form a position-dependent series of measured values. A function can then be fitted to this series, e.g., by means of the least squares method. Printing-related information, e.g., the tone value increase (TVI) can then be derived from the function obtained in this way. In the case of the tone value increase, it is possible, for example, to obtain a more precise computation without the need for more control patches. Accordingly, the system of the invention makes it possible to obtain more precise measurement results with a smaller space requirement and thus at lower expense for the printing operation.

A refinement of the invention provides for the use of a photosensitive sensor that is position-resolving in two directions. Therefore, the measuring device determines a matrix of measured values in the vertical and horizontal directions. In order to obtain a more easily handled amount of data for further computations, the mean value of the measured values in the vertical direction is determined. The measuring device thus computes a series of values consisting of a mean value of all vertical measurements at a horizontal position. An average value that is more reliable for the evaluations is obtained by this measure. A suitable function is then approximated to the series of measured values obtained in this way to make it possible to draw conclusions about the printing process by means of a thorough analysis of this function.

The functional analysis can consist, for example, in determining a point of inflection of the function. On the basis of the position of the inflection point, it is possible, e.g., in the case of the determination of the tone value increase, to determine the position of an abrupt change in tone value. If, for example, a gradient patch with screen tone values of 0 to 100 percent is used, it is possible in this way to make an exact determination of the percent screen tone density at which the abrupt change in tone value occurs. The position of the abrupt change in tone value then makes it possible to draw conclusions about the printing process. For example, an abrupt change in the tone value in the vicinity of the 100 percent screen tone density mark on the gradient patch could mean that somewhat too little fountain solution is being used. This information can then be used in an adjustment step, which, for example, could also take the form of an automatic control. Furthermore, many other functional analyses are possible, such as the slope of the function at the point of inflection. Thus, in accordance with the invention, it is a question, generally speaking, of being able to draw conclusions about the printing process from the analysis of the function.

In accordance with another refinement of the first aspect of the invention, a measuring unit is provided which determines the ink acceptance behavior for each measured value of the series of measured values, for if the measurement is based on a color gradient in the control patch, it is possible to determine a certain color at the individual horizontal positions of the color gradient in advance of the measurement. The measuring device now expects a certain color at each discrete horizontal position. The color densities of the inks are determined, and thus the ink acceptance behavior can be determined by computational methods known from the prior art, as long as it is known which of the inks was printed first in the case of overprinting. Here again, the determined ink acceptance can be compared with a desired value, so that it becomes possible to output a result signal or control signal to appropriate actuators. Furthermore, measured values for generating an ICC profile can be obtained from the measured values, obtained as described above, of one or more control patches that show a gradient or at least partially have a gradient-like form.

Due to the fact that the control patches on the printing medium require less space, which is realized by virtue of the possibility of using gradient patches, a print control strip with smaller control patches of the printing medium in accordance with the invention can be simultaneously printed during the printing operation, which results in space and cost savings for the printing operation. The system of the invention makes it possible to realize automatic control, e.g., for metering fountain solution, by means of the measuring device, which can also be realized in the form of a computer program.

In accordance with the invention, the required gradient limits can be varied as a function of the parameters to be measured. If the gradient patch is a screen tone value gradient, then it is possible, for example, for the determination of the abrupt jump in tone value, to use a high screen tone value gradient range, say, between 80% and 100%. The reason for this is that, at a high tone value, i.e., at a relatively small uncovered area, the supplying of the uncovered area with fountain solution becomes critical, since if there is too little fountain solution, it is precisely the small spaces between the dots that are no longer adequately supplied. Consequently, the fountain solution will no longer reach all areas of the uncovered area, and thus areas that are not actually intended for printing are also covered with ink. An abrupt jump in tone value occurs in the tone value gradient of the control patch. The exact position of the jump in tone value can be read in the tone value gradient.

If, for example, the tendency towards smearing during printing is to be determined, i.e., if it is to be determined whether dot closure occurs during printing, an intermediate tone value range of, for example, 40-60% makes sense. In addition, it is effective to adapt the tone value or color gradient of the control patch in such a way that the dot shapes are adapted to the printing-related measured value to be measured. For example, if dot closure during printing is to be determined, it is advisable to select dot shapes that are especially susceptible to dot closure. For example, they could be squares or rhombi that meet at the vertices.

In accordance with another aspect of the invention, a method is provided, which, in a control patch of the invention, determines both a measured value and a position value for a measuring point of the measured value. To be able to measure with position resolution, a control patch in accordance with the invention is recorded by means of a camera. The printing-related measured value to be determined, for example, the percent area coverage in the case of the determination of the tone value, is measured from the various image sectors of the camera. In addition, however, a determination is also made of the position of each image sector that is viewed and thus the position of the image sector in the gradient to be evaluated in the control patch. With a camera image, the number of viewed image sectors can be varied, so that the amount of information acquired, adapted to the desired measurement, can be increased. If a camera image is not used, the amount of information can also be increased by reducing the distance between the individual measurements. The direction of the gradient in the control patch can be oriented at any desired angle to the printing direction. Moreover, both linear and nonlinear gradient forms are conceivable. The geometric form in which a gradient is arranged in the control patch can be varied in any desired way.

In accordance with a refinement of the method of the present invention, the position values of the measuring points are determined relative to the position of the control patch. If the entire control patch is provided with a gradient, a relationship between a position of the measuring point in the gradient and the measured value measured at the measuring point is obtained with respect to at least one limit of the control patch. This relationship can be represented in a graph by plotting the measured values over the measuring point on a Cartesian coordinate system. To be able to describe the series of measured values that has been obtained in an approximate way by a function, it is useful to perform a fit or a parameter estimate. Conclusions about the process status can then be drawn from the form of the fitted function. In the printing of a tone value gradient up to the full tone, a phase transition can be seen in the function. Starting at the phase transition, the uncovered regions between the dots become filled in, and full tone is printed. In this regard, in accordance with the present invention, it is a matter of the behavior of the function in the region of the phase transition of the fitted function, which has a steeper slope compared to the remainder of the course of the function. The phase transition represents a region in the course of the function that responds especially sensitively to specific process parameters, e.g., the metering of fountain solution. The appearance of the function in this region allows us to draw conclusions about the printing process and especially about the metering of fountain solution.

The determination of the measured values is made during the printing operation of a printing press. Instead of the gradient-like control patches, it is equally possible to use a control strip with gradient-like gradations that consists of control patches with minimal or no distance between the control patches. The number of control patches can be varied according to the desired amount of information. Preferably, a control patch is then smaller than the measuring dot for determining the measured value. To determine the measuring point values in the method of the invention, cameras are generally used for image acquisition. CCD surface chips or CMOS surface chips are especially suitable for this purpose. The acquired image data of the camera is transmitted to an image analysis unit. The aforementioned function of the measured values is determined in the image analysis unit. The aforementioned printing-related measured values can be, for example, a tone value or a colorimetric value.

The tone value function can be used in a series of process parameters. The process parameters concern, on the one hand, the material that is used in the printing press and, on the other hand, the printing conditions during printing in the printing press. By material is meant the blanket, printing ink, printing plate, printing paper, fountain solution, and other printing aids, such as printing oil and printing pastes. Printing conditions are understood to mean especially the conditions in the printing press. The tone value is affected especially by the entities full-tone coloration, compression, press temperature, and the metering of fountain solution.

Generally speaking, correcting variables for the automatic control of the printing operation can be determined from all of the determined measured values. For some measured values, feedback of the measured values to the prepress phase is useful, so that current conditions in the printing press can already be taken into consideration during the processing of the printing job data. In particular, e.g., the amount of fountain solution can be influenced to achieve automatic control of the tone value increase during the printing operation. However, other boundary conditions of the printing process can also be observed, so that, for example, a printing plate diagnosis can be performed by determining a jump in tone value in a low area coverage range of a screen tone value gradient.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 2:
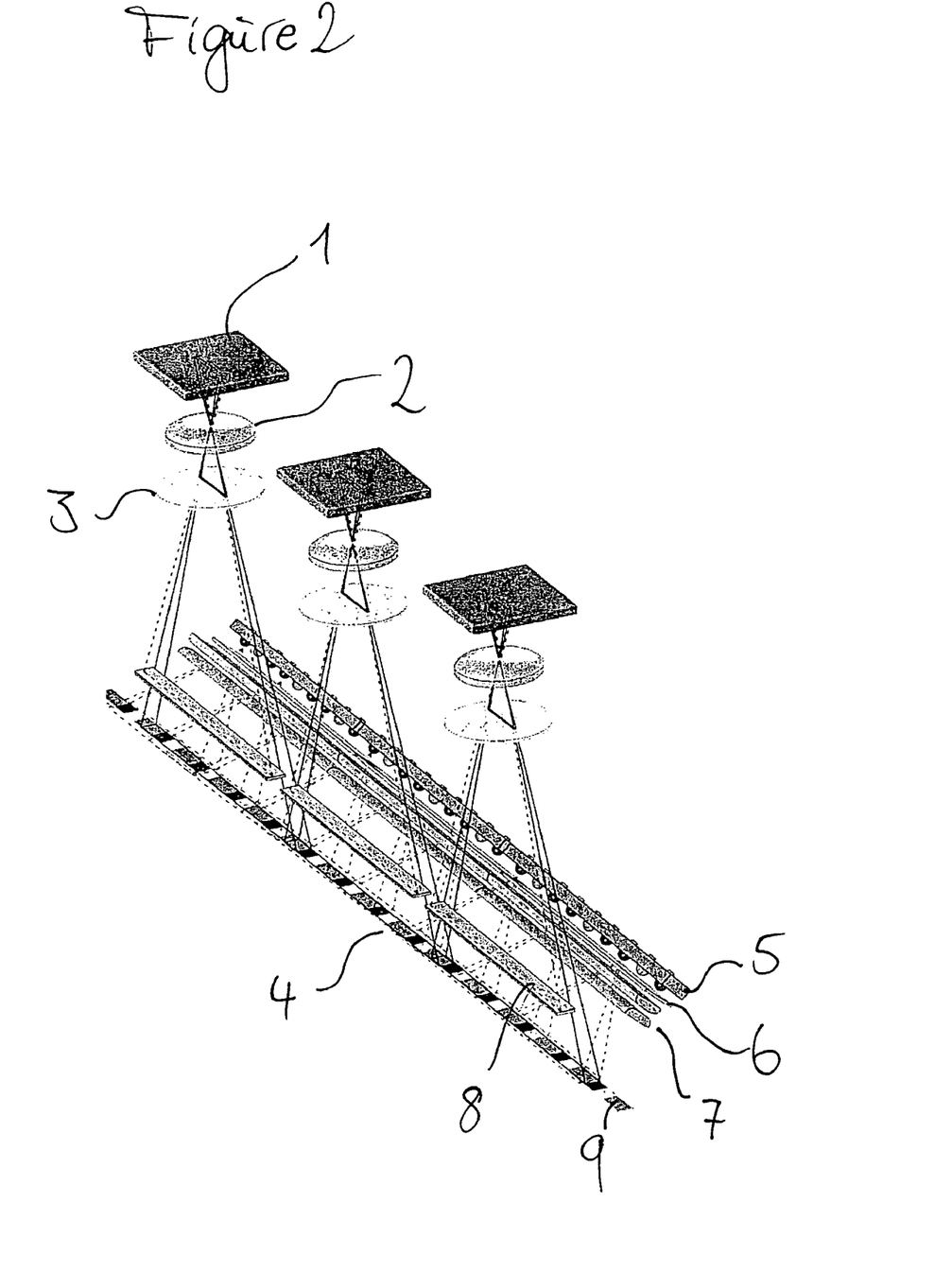
FIG. 2 shows a perspective view of a schematic design of a system of measuring units in accordance with the invention.

FIG. 2 shows three measuring units of the invention arranged side by side, wherein the measuring device is not shown. The illustrated components of the measuring unit of the invention are well known from the prior art and are shown only for purposes of illustration. CCD chip 1 is situated above an optical system 2 for the CCD chip. In addition, a filter 3 is located below the optical system 2. The CCD chips are positioned relative to one another in such a way that they can record the print control strip 4 with mutual overlap, wherein a black aperture array plate 8 is positioned between the filter 3 and the print control strip 4. The print control strip consists of individual control patches 9, wherein no control patch with gradient is shown here. To capture the print control strip, colored LED's 5 are needed, and a filter 6 and an optical system 7 are positioned between the LED's 5 and the print control strip to be illuminated. This design is well known from the prior art and requires no further explanation here.

Figure 3:
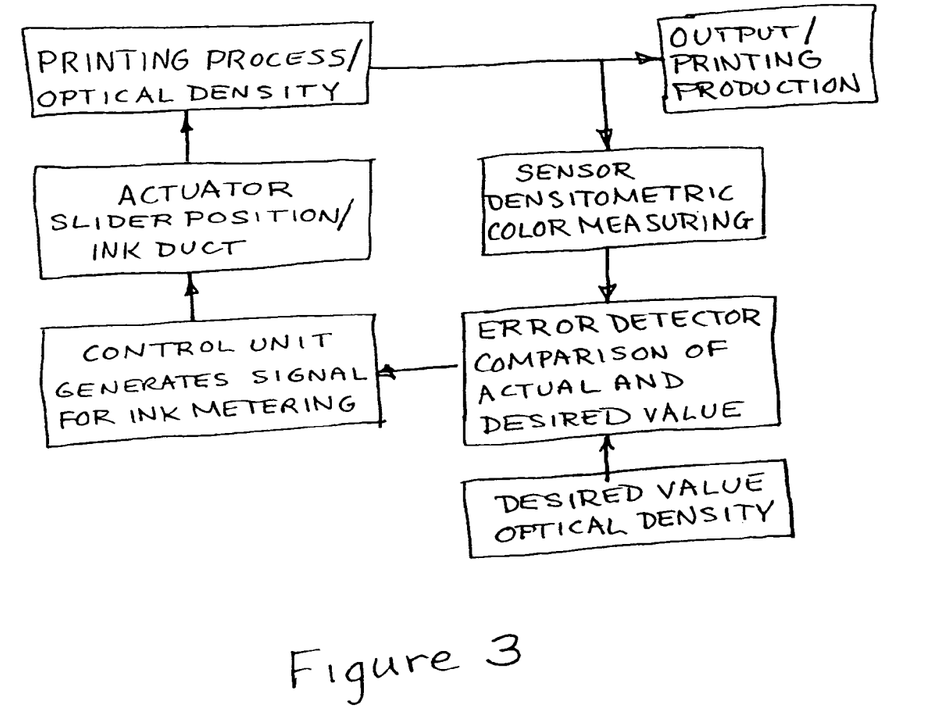
FIG. 3 shows a closed loop of the type that can be carried out by the method of the invention.

FIG. 3 shows a closed loop for automatically controlling the ink metering as it can be realized by the present invention. The actual density of each color in a color gradient can be determined by means of the densitometric color measurement, which is carried out with a densitometer of the invention in a control patch with color gradient, for due to the measurement with position resolution, it becomes possible to assign a specific color to each position in the color gradient. In an error detector, a comparison is then made between the measured actual value of the color density and the preassigned set value of the color density. The error detector outputs an error signal to the control unit, which in turn generates a control signal for the ink metering elements. The actuator then changes, for example, the position of an ink slider, so that the optical density of the corresponding color is changed. The automatic control is performed for each color represented in the color gradient and can be carried out continuously due to the small space requirement for the color gradients.

Figure 4:
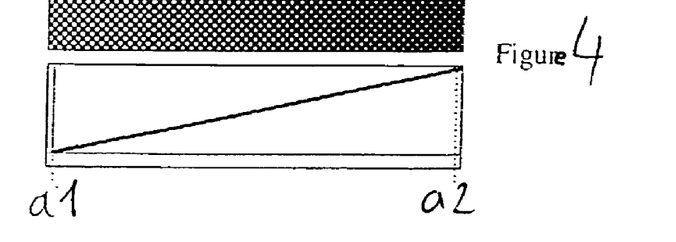
FIG. 4 shows the tone value gradient with area coverage of 80% (a1) to 100% (a2) on the printing form and a corresponding function of the measured values over the measuring position.

FIG. 4 shows a screen tone value gradient on the printing form. As described above, it is similarly possible to have color gradients that also contain mixed colors consisting of suitable color value mixtures of the primary colors used. The fitted function shown under the gradient in FIG. 4 is thus a tone value function, which in the case illustrated here is a linearly increasing function. The slope is constant between the low tone value of 80% (a1) at the left end of the gradient of the control patch and the high tone value of 100% (a2) at the right end of the gradient of the control patch. In order to measure certain printing process parameters, it is useful, as has already been explained, to select suitable limits of the gradient. In the present case, to determine the tone value increase, the limits 80% and 100% screen tone value were selected. The exact determination of the tone value increase is very important in the printing process. If, for example, the tone value increase of the primary colors used is not determined precisely, then likewise it is possible to make only an imprecise adjustment of the tone value increase of the primary colors. If the tone value increase of one color is, for example, higher than that of another color, the color balance is disturbed, and a color cast develops.

Figure 5:
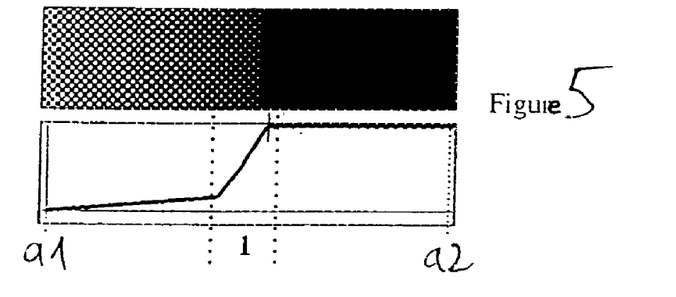
FIG. 5 shows a typical camera recording of the tone value gradient from FIG. 4 in the production run and a corresponding function of the measured values over the measuring position.

FIG. 5 shows a camera image of a gradient in the production run with the gradient limits selected in FIG. 4 and the behavior of a function of the determined series of measured values. To determine a suitable mathematical model and thus a suitable course of the function for the determined series of measured values and especially for the phase transition, it is necessary to fit a suitable function, e.g., by the least squares method. The transition from the screened area to an area without screening is clearly visible both in the camera image and in the behavior of the function. In the context of the invention, this transition is called the phase transition. In the course of the function in FIG. 5, the phase transition can be identified by the sharply increasing tone values, i.e., the greater slope in the course of the function. If this region is viewed in a section with a previously determined width (see dotted vertical line), a characteristic functional pattern is obtained for a phase transition.

Conclusions about process status can be drawn from the functional pattern in the phase transition, e.g., by determining the point of inflection and slope of the function in this region. The tone value range shown in FIG. 5 of 80% to 100% is suitable especially for metering the amount of fountain solution.

Figure 6:
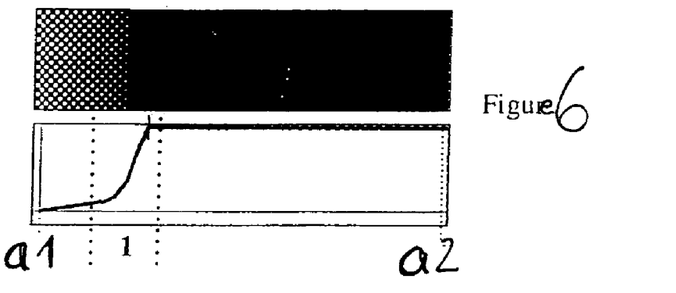
FIG. 6 shows a camera recording of the tone value gradient in the production run, wherein the determined phase transition appears in a lower tone value range, and a corresponding function of the measured values over the measuring position.
Figure 7:
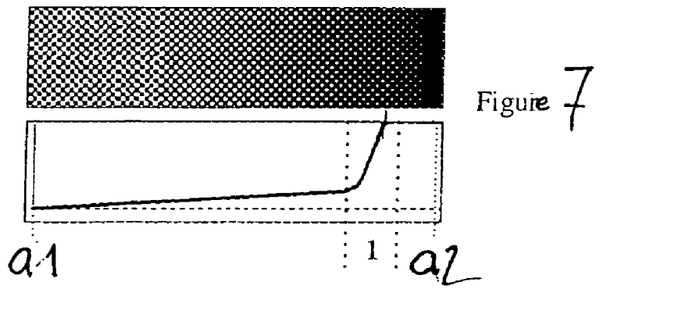
FIG. 7 shows another camera recording of the tone value gradient in the production run, wherein the determined phase transition now appears in a very high tone value range, and a corresponding function of the measured values over the measuring position.

FIG. 6 shows the same tone value range as FIG. 5, but the phase transition is located farther to the left, i.e., closer to 80% area coverage. The course of the function in the phase transition is also different. A tendency towards smearing during printing, for example, can be read from functional behavior of the type shown in FIG. 6. Accordingly, open-loop or closed-loop control in this case would increase the amount of fountain solution until the phase transition returns to the desired range, i.e., until the function follows a course as shown in FIG. 5. FIG. 7 shows a process status that is the opposite of that shown in FIG. 6, i.e., the amount of fountain solution is adjusted too high here, and the phase transition occurs in the vicinity of 100% area coverage in a region on the right in the function.

Figure 8:
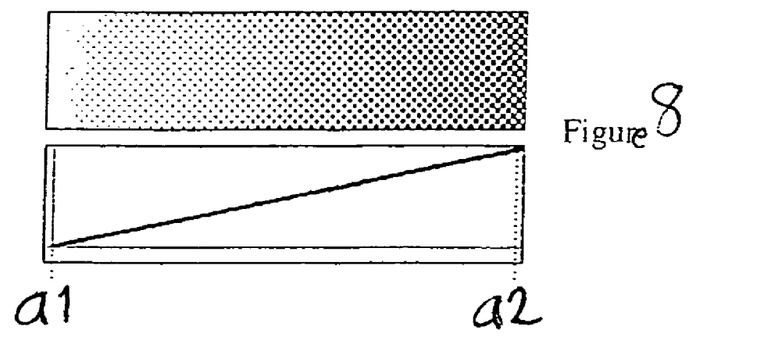
FIG. 8 shows a tone value gradient on the printing form in an area coverage range of 0% to 10% and a corresponding function of the measured values over the measuring position.

The tone value gradient that is shown in FIG. 8 is intended for checking the production stability of a printing form or printing plate during printing. This is accomplished by establishing the limits of the tone value range at 0% and 10%. FIG. 8 shows the gradient as it is applied on the printing form. The dot sizes in this tone value range are very small. For this reason, the wear of a printing plate can be detected on the basis of the disappearance of the smallest dots in the left region of the tone value gradient.

Figure 9:
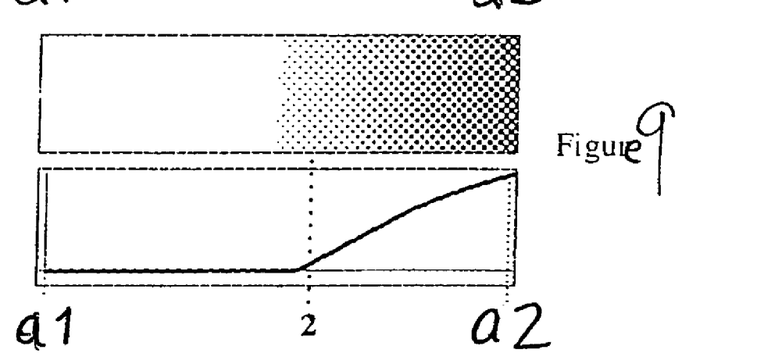
FIG. 9 shows a camera recording of the tone value gradient with limits as in FIG. 8, wherein this camera recording was made at the beginning of the printing production, and a corresponding function of the measured values over the measuring position.

FIG. 9 shows a recording of the tone value gradient at the beginning of the printing production of a printing plate. It is readily apparent that the left region of the tone value gradient is already completely white, i.e., the smallest dots are already worn down and have disappeared. In regard to the course of the function in FIG. 9, this results in a straight line with a slope of 0 in the region of the worn dots.

Figure 10:
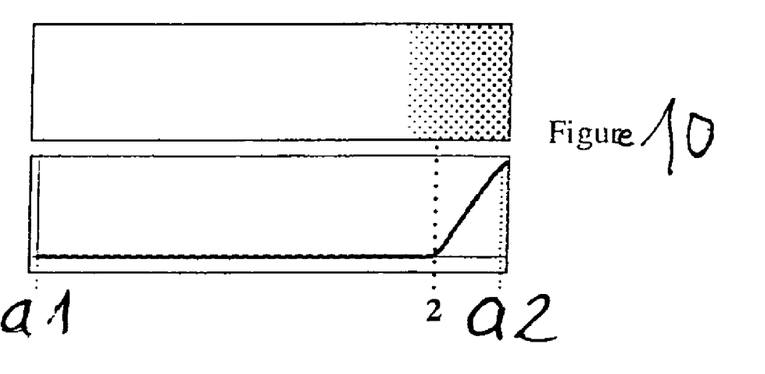
FIG. 10 shows a camera recording of the tone value gradient already described in FIGS. 8 and 9, but in this case near the end of the service life of the printing form, and a corresponding function of the measured values over the measuring position.

FIG. 10 shows a tone value gradient near the end of the printing production of a printing plate. It is readily apparent that the zero line of the course of the function is lengthened, but the course of the function in the phase transition has also changed. In this example as well, conclusions can be drawn about process states of the printing process both from the form of the phase transition with reference to a characteristic width and by determination of various function characteristics, such as slope, point of inflection, or extrema.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A measuring unit for determining a printing-related measured value from at least one of a tone value gradient and a color gradient of a control patch printed on a printing medium, the measuring unit comprising:
   a photosensitive sensor that can resolve a position in the control patch in at least one direction, said sensor producing image data;
   a central processing unit for evaluating the image data from the photosensitive sensor;
   a measuring device for determining a printing-related measured value at a measuring point in the control patch and determining a position of the measuring point; and
   a memory for storing the measured values,
   wherein the printing-related measured value and the position of the measuring point are determined during a printing operation of a printing press.

2. The measuring unit of claim 1 wherein the measuring device determines at least one limit of at least one of said tone value gradient and said color gradient of said control patch, and determines the position of the measuring point with reference to this limit.

3. The measuring unit of claim 1 wherein the measuring device determines a series of measured values as a function of the position of the measuring point, and fits a suitable function to said series of measured values.

4. The measuring unit of claim 3 wherein the measuring device determines an inflection point of the function and possibly a slope of the function at the inflection point.

5. The measuring unit of claim 3 wherein the measuring unit determines an ink acceptance behavior for each measured value of the series.

6. The measuring unit of claim 1 wherein
   the photosensitive sensor can resolve a position in two directions; and
   the measuring device determines a matrix of measured values in horizontal and vertical directions, and determines a mean value of the measured values in the vertical direction, so that a position-dependent series of averaged measured values is obtained.

7. The measuring unit of claim 1 wherein the measuring device compares at least one measured value with a predetermined limit and outputs suitable result signals and/or control signals.

8. The measuring unit of claim 1 wherein the measuring device performs densitometric measurements.

9. The measuring unit of claim 1 wherein the photosensitive sensor is one of a CCD surface chip and a CMOS surface chip.

10. The measuring unit of claim 1 wherein the measuring device comprises a computer program.

11. A method for determining a printing-related measured value of a printing press, the method comprising:
    providing a printed medium having a control patch printed by the printing press with at least one of a tone value gradient and a color gradient;
    determining a printing-related measured value from at least one of said tone value gradient and said color gradient of said control patch; and
    determining the position in the control patch of a measuring point associated with said measured value,
    wherein the steps of determining the measured value and determining the position are performed during a printing operation of a the printing press.

12. The method of claim 11 wherein the position of the measuring point is determined with respect to the position of the control patch.

13. The method of claim 11 comprising:
    determining a series of measured values as a function of the position of the measuring point.

14. The method of claim 11 comprising:
    determining a matrix of measured values in horizontal and vertical directions; and
    determining a mean value of the measured values in the vertical direction, so that a position-dependent series of averaged measured values is obtained.

15. The method of claim 11 comprising determining said printing-related measured value from a control strip having gradient-like gradations consisting of a plurality of contiguous control patches.

16. The method of claim 11 comprising determining the measured value by image acquisition from one of a CCD surface chip and a CMOS surface chip.

17. The method of claim 11 further comprising computing an ICC profile from the printing-related measured value.

18. The method of claim 11 further comprising computing a tone value increase from the printing-related measured value.

19. The method of claim 11 further comprising computing a correcting variable for one of open-loop and closed-loop control from the printing-related measured value.

20. The method of claim 19, further comprising controlling a fountain solution based at least in part on the correcting variable.

21. The method of claim 11 wherein the control patch is printed with a screen tone value gradient.

* * * * *